Figure 1:
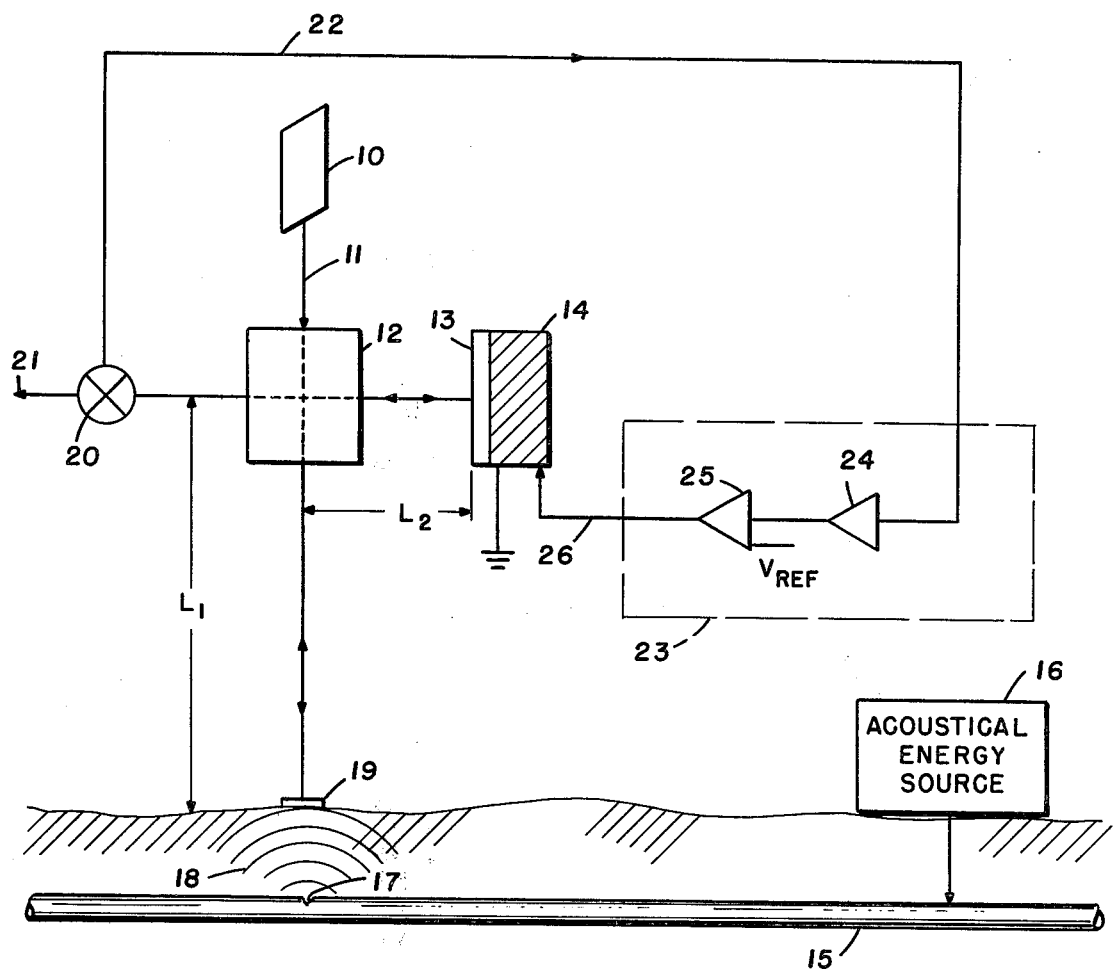

United States Patent [19]

Murphy et al.

[11] 4,172,382
[45] Oct. 30, 1979

[54] LASER INTERFEROMETRY DETECTION METHOD/APPARATUS FOR BURIED STRUCTURE

[75] Inventors: John C. Murphy, Columbia; Raymond C. Cole, Baltimore, both of Md.

[73] Assignee: The Johns Hopkins University Applied Physics Laboratory, Laurel, Md.

[21] Appl. No.: 948,292

[22] Filed: Oct. 3, 1978

[51] Int. Cl.² .............................................. G01M 3/04
[52] U.S. Cl. ..................................... 73/40.5 A; 73/655
[58] Field of Search .............. 73/40.5 A, 40.5 R, 49.5, 73/591, 655, 656, 657

[56] References Cited
U.S. PATENT DOCUMENTS 3,264,864  8/1966  Reid et al. ...................... 73/40.5 A
4,086,808  5/1978  Camac et al. ....................... 73/655

FOREIGN PATENT DOCUMENTS 214978  6/1968  U.S.S.R. ............................... 73/40.5 A

*Primary Examiner*—Donald O. Woodiel
*Attorney, Agent, or Firm*—Robert E. Archibald

[57] ABSTRACT

The present invention relates generally to the utilization of laser interferometry for performing detection of buried structures such as underground natural gas pipeline. More specifically, the invention relates to the use of a laser interferometer system for detecting leaks and similar defects, such as corrosion, in buried pipelines, pressurized containers or other metallic structures, based upon the sensing of subnanometer earth surface displacements produced by elastic waves which are emanated from the leak or defect and propagate in the surrounding earth medium.

10 Claims, 3 Drawing Figures

LASER INTERFEROMETRY DETECTION METHOD/APPARATUS FOR BURIED STRUCTURE

BACKGROUND AND RELATED PRIOR ART

Optical wavelength interferometry has long been recognized as a method for precise length determination. For example, interferometrically controlled machine tools have been utilized in highly specialized manufacturing operations, including production of difraction gratings, for several decades. In these cases, the scale of the distances measured was of the order of the fringes produced by the interference between the reference and signal light beams, i.e. for visible light, the scale was of the order of one hundred nanometers. Such measurements have been exclusively laboratory measurements, however, with great care taken to provide environmental control against unwanted vibration, as well as changes in the ambient temperature, humidity and related factors.

With the advent of the laser and its greater coherence length, the qualitative aspects of the interferometry measurement technique did not change. Now technical problems arose, however, associated with maintaining equal path lengths in the interferometer beam channels or arms. The use of a laser interferometer to measure time-varying displacements has been widely recognized, and descriptions of laboratory type laser interferometers have been published by S. M. Khana et al, 44 J. Acoust. Soc. Am. 1555(1968); P. R. Dragsten et al. 60 J. Acoust. Soc. Am. 665(1976); and R. M. De LaRue et al, 119 Proc. IEE (1972).

DESCRIPTION OF THE INVENTION

In accordance with the present invention, it is proposed that laser interferometry be utilized for the purpose of detecting leaks and other defects in buried structure such as underground pipelines. This is accomplished by creating an elastic wave which emanates, for example, from the pipeline, at the leak, and propagates through the surrounding earth to produce time-varying displacements of the earth's surface. These displacements are then detectable by a portable laser interferometer system, proposed in accordance with the present invention, without requiring mechanical connection to the earth.

The present invention thus obviates the need for accelerometers or similar motion sensors which must be attached to the earth and are thereby subject to reduced sensitivity with increasing frequency, brought about by the inertial loading of the earth by the mass of the sensor, and the associated problem of distinguishing between the various directional components of the earth's motion when the sensor is rigidly connected through the earth's surface. The proposed laser interferometer sensor is thus non-contacting and does not require physical attachment to the surface under investigation; i.e. during measurement of small earth vibrations produced by energy emanating from a pipeline leak or other defect, for example.

In light of the above, a general object of the present invention is to utilize laser interferometry for detecting minute earth displacements produced by elastic waves emanating from a buried structure, such as a pipeline, for such purposes as detecting leaks and other defects.

Another object of the present invention is to provide a method and apparatus, employing a laser interferometric system, capable of detecting leaks in a buried pipeline, by sensing sub-nanometer earth surface displacements produced by acoustical waves emanated from a leak.

Another object of the present invention is to accomplish detection of leaks in buried pipeline, while obviating the need for accelerometers or similar sensing devices which must be attached to the earth. The present invention thus provides a portable leak detector which can, in practice, be used in a setting other than the controlled conditions of a vibrationally isolated table and environmentally controlled room.

A further object of the present invention is to provide a heterodyne type laser interferometer employing active stabilization of the phase of the translation frequency, through the use of electronic circuitry, to achieve the operational advantages of rapid detection, capability of handling both large and small amplitude displacement signals, and relative system simplicity in terms of the number and complexity of its components.

Figure 2:
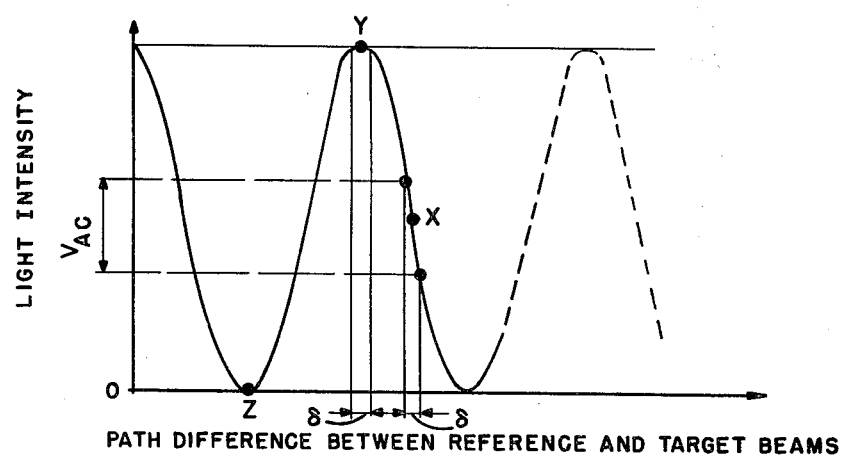
Figure 3:
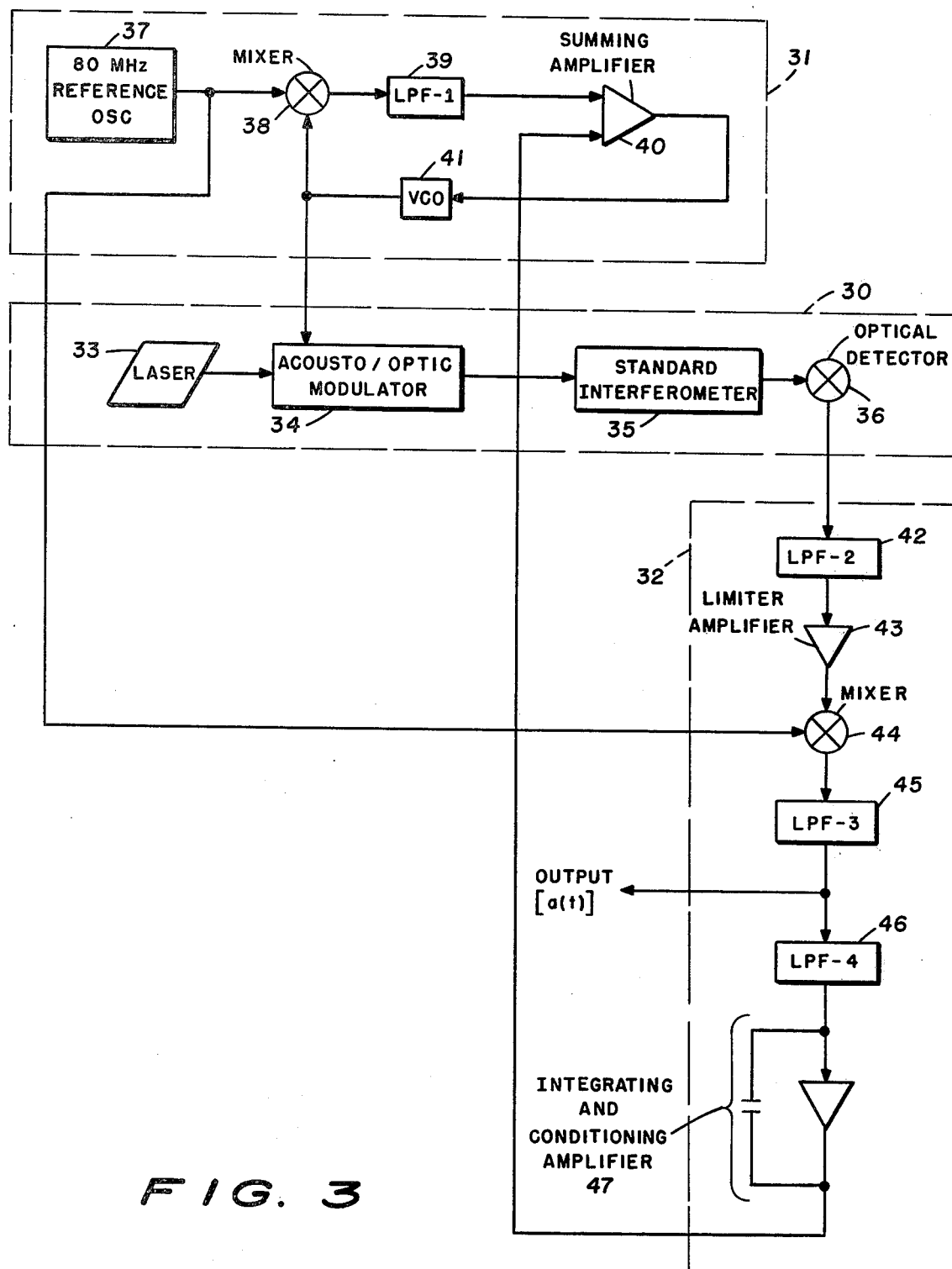

Other objects, purposes and characteristic features of the present invention will in part be pointed out as the description of invention progresses and in part be obvious from the accompanying drawings wherein:

FIG. 1 is a generalized block diagram of one embodiment of the present invention utilizing a homodyne laser interferometer of the in-line or Fizeau configuration, with an electronically controlled piezoelectric displacer for stabilizing in the instantaneous laser reference beam path length;

FIG. 2 is a curve illustrating the way in which light intensity from the optical detector output varies as a function of path length difference, characteristic of two-beam interferometers; and FIG. 3 illustrates, in block diagram form, a second embodiment of the present invention employing a heterodyne interferometer system employing a high frequency phase locked loop and associated electronic circuitry to control the frequency and phase of the optical signal entering the reference channel of the laser interferometer.

As displacement detectors, laser interferometers rely on the observation that time-dependent changes in the optical path length of the laser signal path within the interferometer induce phase modulation of the signal output from the optical detector. A general expression for the output current from the optical detector, normalized to unit intensity in the reference and signal beams, which is applicable to both the homodyne and the heterodyne laser interferometers, is given by the equation $$i_D = 2(1 + \cos[(p-g)\omega_B t + \frac{4\pi}{\lambda_0}(L_2 - L_1) - \frac{2\omega}{C} B(pL_1 - gL_2)] \quad \text{(Eq. 1)}$$

In this expression, $L_2$ and $L_1$ are the reference and signal path lengths respectively, $\omega_B$ is the translation frequency (in radians), p and g are integers equal to 0, ±1, and $\lambda_0$ is the wavelength of the unshifted optical beam. A time-varying change $\delta(t)$ in the laser signal path length $L_1$ associated both with the displacement under study and with spurious sources such as noise or drift related changes n(t) in the relative path length $L_2-L_1$ may be represented in Eq. 1 as $$i_D = 2(1 + \cos[(p-q)\omega_B t + \frac{4\pi}{\lambda_0}(L_2^0 - L_1^0) + \frac{4\pi n(t)}{\lambda_0} - \frac{4\pi\delta(t)}{\lambda_0} - \frac{2\omega}{C} B(pL_1 - gL_2)]) \quad \text{(Eq. 2)}$$

For the homodyne laser interferometer, $p=g=0$ and $$i_D = 2(1 + \cos[\Omega_0 + \Delta\Omega(t) - \frac{4\pi\delta(t)}{\lambda_o}]), \quad \text{(Eq. 3)}$$

with $\Omega_o$ and $\Delta\Omega_o(t)$ being the second and third terms in the brackets of Eq. 2.

For the heterodyne laser interferometer, where only the referencebeam is translated, $p=1$ and $g=0$ and $$i_D = 2(1 + \cos[\omega_B t + \Omega_0 + \Delta\Omega_0(t) - \frac{4\pi\delta(t)}{\lambda_0}]), \quad \text{(Eq. 4)}$$

it being noted that in writing Eq. 4, the term $$\frac{2\omega_B L_1}{C}$$

in Eq. 3 was dropped.

Referring now to the homodyne embodiment illustrated in FIG. 1 of the drawings, a suitable laser 10, of a helium-neon single mode type, for example, operating at an output frequency of approximately $10^{14}$Hz. directs its output beam 11 to a beam splitter 12 which divides the laser beam into beams; one of which is directed to impinge upon a mirror 13 mounted on a piezoelectric displacer 14. This beam serves as the reference channel for the homodyne laser interferometer and the reference path length is designated as $L_2$ in FIG. 1. The other or signal beam from the beam splitter 12 is directed toward the ground, in FIG. 1, for the purpose of detecting displacements of the earth's surface associated with a leak (or similar defect) to be detected in buried pipeline 15.

A source of acoustical energy 16 is connected to supply its energy to the pipe 15 and thereby generate an elastic wave, at acoustical frequency, emanating from the leak 17 and propagating through the earth medium as designated at 18. In order to sense the minute vibrational displacements at the earth's surface produced by the elastic wave 18, a suitable mirror 19 is shown disposed on the earth's surface to reflect the laser signal beam. It should be understood here that the mirror 19 is shown by way of example only and that the earth typically contains sufficient background reflection so that, for most practical applications, a separate mirror may not be required in order to obtain adequate signal beam reflection from the earth's surface. In any event, the signal beam reflected back to the beam splitter 12 combines with the reference beam deflected from the mirror 13 and the resultant is applied to the optical detector 20 which produces a corresponding signal 21 whose intensity varies in accordance with the vibrations detected at the earth's surface. Moreover, it should be understood at this time that the phrase elastic wave, as used herein, refers to any vibrational or mechanical wave which can propagate in a solid or fluid medium, and includes both compressional and shear waves as specific examples. Also, the term acoustical as used herein refers not only to compressional wave propagation but also to propagation involving compressional and shear waves. Thus, in the case where the pipeline 15 carries natural gas, the acoustical source 16 would produce compressional waves within the gas which would be converted to elastic wave 18 at the leak; whereas, where the pipeline 15 carries a liquid capable of supporting both compressional and shear waves, the acoustical source 16 would produce both types of waves in the liquid to generate the elastic wave 18 at the leak. It should therefore be clear that the source 16 may have various frequencies, power output, etc. depending upon the requirements of practice.

Referring now to FIG. 2 of the drawings, the manner in which the output light intensity from the optical detector 20 varies as a function of path difference between the reference and signal beams $(L_2-L_1)$, is represented. In order to assure that the laser interferometer will operate at the point of maximum displacement sensitivity, namely at point x in FIG. 2, suitable stabilization electronics are provided in FIG. 1 and comprise a feedback loop which responds to an error signal picked off the optical detector 20 and fed back, along line 22, to conventional stabilization electronics unit 23 which comprises a lock-in amplifier 24 and a high voltage driver amplifier 25. The stabilization electronics unit 23 responds to and compares the error signal 22 against a preselected voltage reference and applies a control voltage 26 to the piezoelectric displacer 14, effected to move the reference beam mirror 13 and thereby maintain the path difference at the desired maximum sensitivity operating point X.

For a more thorough understanding of the operation of the FIG. 1 embodiment, reference is again made to Eq. 3 pertaining to the homodyne laser interferometer system, wherein the expression within the brackets; namely, $$\Omega_0 + \Delta\Omega_0(t) - \frac{4\pi\delta(t)}{\lambda_0} = \phi(t) \quad \text{(Eq. 5)}$$

represents the instantaneous phase difference between the signal and reference beams of the interferometer. As noted earlier, in accordance with the present invention, the object is to determine $\delta(t)$ or $$a(t) = \frac{4\pi\delta(t)}{\lambda_0};$$

that is, the earth displacement produced by the elastic wave 18 resulting from the pipe leak 17 represented in FIG. 1. Since the variable term in Eqs. 3 and 5 is $\cos\phi = \cos\Omega_o'(t)\cos a(t) + \sin\Omega_o'(t) \sin a(t)$, which for
$a(t) << 1$ becomes
$\cos\phi = \cos\Omega_o'(t) + \sin\Omega_o'(t) a(t)$, \quad (Eq. 7)

one method of displacement detection using homodyne laser interferometers involves maintaining $\sin\Omega_o'(t) \approx 1$.

In the embodiment shown on FIG. 1 of the drawings, the closed loop feedback through stabilization unit 23 controls $\Omega_o'(t)$ via the piezoelectric displacer 14. More particularly, as is well known, such displacers are utilized to change lengths upon application of a control voltage and, as applied to the present interferometer system, the mirror 13 in the reference beam channel is adjusted in accordance with the feedback signal appearing on line 22, in order to vary the instantaneous reference path length and cause the operating point for the laser system to coincide with the point of maximum sensitivity (point X in FIG. 2.). An alternate method of controlling $\Omega_o'(t)$ involves separating $\cos\Omega_o'(t)$ in Eq. 6 from $\sin\Omega_o'(t)$ a(t) by frequency domain filtering and then using $\cos\Omega_o'(t)$ directly as an error signal. This latter method of stabilization is somewhat restricted in application, however, since it assumes the time variation of n(t) is slow relative to a(t).

It should be understood at this time that, in accordance with the present invention, it is contemplated that the acoustical energy source 16 in FIG. 1 may be replaced with alternate ways of generating an elastic wave emanating from the leak or defect to be detected. By way of example, the internal pressurization of the pipeline may be selected to produce the elastic wave, represented at 18, emanating from the defect 17. Other possible alternatives for generating the elastic wave include the use of such well-known phenomena as: electro-striction (the stretching or shrinking of the material under the influence of an implied electric field); magneto-striction; or possibly even stress corrosion cracking (the generation of sound by the release of internal strain).

As noted early, FIG. 3 of the drawings illustrates a second but preferred embodiment, utilizing a heterodyne type laser interferometer system proposed in accordance with the present invention. However, before describing this second embodiment in detail, further background discussion will be presented regarding heterodyne laser interferometers, assuming that class of heterodyne systems in which only one beam (either signal or reference) is frequency translated; it being understood and well-known that a fully analogous treatment can be given for the symmetrical case wherein both beams are translated.

The preceeding Eq. 4 applicable to such heterodyne systems may be reqritten as $$i_D = 2(1 + \cos[\omega_B t + \phi(t)]) \qquad \text{(Eq. 8)}$$

where $\phi(t)$ as defined in Eq. 5 is a phase modulation of the translation frequency $\omega_B$. Since $\omega_B$ is commonly in the radio frequency range, $$Q(t) = \cos[\omega_B t + \phi(t)] \qquad \text{(Eq. 9)}$$

is readily separated from the DC component of the optical detector output current ($i_D$).

Various methods involving frequency discrimination, phase demodulation of frequency domain filtering have been described in the open literature in relation to heterodyne laser interferometer which allow the displacement a(t) term to be extracted from the $\phi(t)$ term in Eq. 9. However, each of these previously proposed methods have limitations making them applicable only to special cases. For example, the frequency domain filtering methods previously proposed are restricted to cases where a(t)<<1, which for a helium-neon laser implies $|\delta(t)| < 400\text{Å}$. Vibrational amplitudes greater than this are commonly observed and thus limit the applicability of this particular method. The frequency demodulation technique suffers a threshold effect similar to that observed in FM communications receivers which sets a relatively large minimun detectable displacement, $\delta \text{min} \sim 3\text{Å}$. This is a severe limitation in leak detection where small displacements need to be detected against a larger background.

Many of the limitations attendant to such previously proposed techniques are eliminated in the heterodyne laser interferometer system configuration shown in FIG. 3, as a second embodiment of the present invention. Specifically, the proposed heterodyne laser interferometer system comprises an optical subsystem 30; a high frequency phase locked loop 31; and feedback and detection electronics unit 32, which cooperate to control the instantaneous phase of the optical signal entering the reference channel for the interferometer.

In accordance with the present invention, the optical subsystem 30 comprises a helium-neon laser 33 which directs its output to a conventional acousto/optic modulator unit 34 where the laser output signal is frequency translated in accordance with well-known practice. The output of the modulator 34 is applied to a standard interferometer 35 which may be of the Michaelson, Fizeau or other well-known configuration and whose output is applied to optical detector 36. The interferometer 35 essentially (a) divides its input light signal into reference and signal beams, (b) operates on the two beams independently including directing the signal beam onto the earth's surface (see FIG. 1) from which it is reflected back to the interferometer, and (c) coherently combines the reference and reflected signal beams, so that the output of optical detector 36 is indicative of the earth's displacements to be detected.

The high frequency phase locked loop 31 comprises: an eighty MHz reference osillator 37, mixer 38, low pass filter 39, summing amplifier 40 and a voltage controlled oscillator (VCO) 41 which responds to the output of the summing amplifier 40. VCO 41 applies its output as the second input to the mixer 38 of the phase locked loop, as is conventional practice, and in accordance with this invention also applies its output as a control for the acousto/optic modulator 34.

The feedback and detection electronics module 32 responds to the output from the optical detector 36 and includes a low pass filter 42 whose output is applied, via limiter amplifier 43, to mixer 44. The outher input to the mixer 44 is the eighty MHz output from reference oscillator 37. The output of mixer 44 is, in turn, applied to a serial pair of low pass filters 45 and 46. The output of filter 46 is applied to an integrating and conditioning amplifier circuit 47 which feeds back its output as an error signal to the summing amplifier 40 in the high frequency phase locked loop 31; whereby, the reference path or channel for the laser interferometer is translated in frequency by the eighty MHz reference signal, but with an instantaneous phase stabilized relative to the signal path by the voltage output signal from the integrating and conditioning amplifier 47. The function of the module 31 is thus to generate a reference channel optical signal in the interferometer 35, translated in frequency by $\omega_R$ (in Eq. 1, $\omega_B = \omega_R$); i.e. the 80 MHz frequency of the reference oscillator 37, but with an instantaneous phase $\phi'(t)$ determined by the control voltage input to the summing amplifier 40 from the integrating and conditioning amplifier 47 in module 32.

As indicated by Eq. 8 above, the output of the optical detector 36 is at the translation frequency ($\omega_R = 80$ MHz) and contains phase modulation $\phi(t)$ given by the expression $\phi'(t) - \Omega_o'(t) - a(t)$. This detector output signal enters module 32 and is first applied to low pass filter 42 which rejects the second harmonic (160 MHz) of the translation frequency. A limiter amplifier 43 then removes any amplitude modulation from the signal and applies it to mixer 44, where it is combined with the output of the reference oscillator 37 so as to remove the 80 MHz translation frequency. Following passage through the low pass filter 45, to assure rejection of the second harmonic of the translation frequency, the low pass filter 46 separates the temporally slow components of $\Omega_o'(t)$ from the faster components of $\Omega_o'(t)$ and a(t). Assuming that the total time variation of $\Omega_o'(t)$ is slow relative to a(t), the output of the integrating and conditioning amplifier 47 is a voltage $V_E = K[\phi'(t) - \Omega_o'(t)]$ corresponding to spurious phase modulations. When placed in a closed loop, with $V_E$ used as the input to the summing amplifier 40 (with appropriate polarity), the condition for loop closure is $\phi'(t) - \Omega_o'(t) = 0$, at which time the output signal from the low pass filter 45 becomes approximately equal to a(t).

In accordance with the second embodiment of the present invention, the control voltage $V_E$ is fed back to the summing amplifier 40 and thereby controls the acousto/optic modulator 34, via VCO 41, to impart instantaneous phase change to the translated laser optical signal corresponding to the expression $\phi'(t) - \Omega_o'(t)$; whereby unwanted phase modulation due to spurious sources such as noise and drift are compensated for and whereby, at the output of the low pass filter 45, an output signal may be extracted indicating very precisely the quantity a(t); i.e. the ground displacements to be detected.

Resulting from the proposed use of active stabilization of the phase of the translation frequency $\omega_B = \omega_R$, as just described, and the use of a voltage controlled phase modulator built around the oscillator drive of the acousto/optic modulator 34, the second embodiment of the present invention shown in FIG. 3 has the operational advantages of:

(a) the system is fast since the stabilization time of a loop built around an acousto/optic modulator is several orders of magnitude faster than those using piezoelectric displacers;

(b) the system can handle large and small amplitude signals, i.e. $a(t) \lesssim 1$; and (c) the system is relatively simple in terms of the number and complexity of its components.

The present invention thus provides for the detection of leaks and other defects in buried structure, such as underground natural gas pipeline, by using laser interferometry to detect minute earth displacements resulting from and identifying the leak. The proposed detection method and apparatus is particularly advantageous in that it does not necessitate physical attachment to the earth surface under investigation; i.e. the proposed apparatus can be portable. Moreover, elimination of the need for physical attachment renders the present invention amenable to the employment of pattern recognition methods for characterizing the signature of the leak-radiated acoustical signal wave from that due to environmentally related sound or interfering sound signals from the walls of the pipe, as well as other artifacts experienced in practical application.

Various other modifications, adaptations, and alterations are of course possible in light of the above teachings. It should therefore be understood that within the scope of the appended claims, the invention may be practiced otherwise than as specifically described hereinabove.

What is claimed is:

1. A method for detecting defects in a buried structure comprising the steps of:

generating an elastic wave emanating from said structure in the vicinity of said defect and propagating through the surrounding medium towards a surface of the medium, and, detecting displacement of the medium surface resulting from said elastic wave impinging upon said surface, the step of detecting surface displacement comprising the steps of:

directing a laser signal beam at the surface, reflecting the signal beam at the surface, combining the reflected signal beam with a reference beam from the laser beam, and detecting the time varying phase difference between said reflected signal and said reference beams produced by said surface displacement.

2. The detection method specified in claim 1 wherein the step of generating said elastic wave comprises connecting an energy source to the buried structure selected to produce elastic waves of predetermined characteristic emanating from said structure in the vicinity of said defect.

3. The detection method specified in claim 2 wherein said buried structure is a fluid container with potential leaks and wherein the step of connecting an energy source to said container comprises the application of an acoustical signal which propagates through the fluid within said buried container structure.

4. The detection method specified in claim 3 wherein the buried structure is an underground fluid pipeline and the step of generating an elastic wave comprises application of an acoustical energy source to propagate acoustical energy through the pipeline fluid to generate an elastic wave at acoustical frequency emanating from the pipeline at a leak location.

5. A system for detecting defects in buried structure comprising, in combination, means for generating an elastic wave emanating from said buried structure at said defect and propagating within the surrounding medium towards the surface of said medium, and, means for detecting displacement of the medium surface resulting from impingement thereon of said elastic wave, said detection means including a laser interferometer having an optical detection means for producing an output signal indicative of said surface displacement.

6. The detection system specified in claim 5 wherein said laser interferometer includes, means for producing, operating on and coherently combining reference and signal laser beams, said signal laser beam being directed towards and reflecting from said medium surface, and means for stabilizing the reference beam of said laser interferometer to maintain operation at a point of maximum displacement sensitivity.

7. The detection system specified in claim 6 wherein said laser interferometer is of the homodyne type having a reference mirror disposed in and defining the length of the reference laser beam path and further including, stabilization means comprising a piezoelectric displacer supporting said reference beam mirror and, circuit means responsive to the output of said optical detection means for applying a control voltage to said piezoelectric displacer effective to vary the length of said reference laser beam path for stabilizing said interferometer to operate at a point of maximum detection sensitivity.

8. The displacement detection system specified in claim 6 wherein said laser interferometer is of the heterodyne type comprising, a laser source an optical interferometer for dividing the output of said laser source into reference and signal laser s, said interferometer operating independently on each of said reference and signal laser beams and coherently combining such beams following reflection of said signal beam from said medium surface, an optical detector responsive to said combined laser beams for producing an output signal indicative of surface displacement, and means for controlling the reference laser beam to have a stabilized instantaneous phase relative to said signal beam.

9. The detection system specified in claim 8 wherein said control means comprises, a translator means interconnecting the output of said laser source to said optical interferometer for translating the output of said laser source by a predetermined frequency, a phase locked loop connected to said translator means and including, a reference oscillator generating an output signal at said predetermined frequency, a mixer connected operably to the output of said reference oscillator, and a voltage controlled oscillator connected to said mixer means for generating a frequency corresponding to that of said reference oscillator, and further including means responsive to the output of said optical detection means for applying a control voltage to said voltage controlled oscillator to cause the output of said voltage controlled oscillator to have stabilized instantaneous phase relative to the reflected laser , said voltage controlled oscillator being connected to control said translator means.

10. The detection system specified in claim 9 wherein the combined reference and reflected laser s contain a first phase modulation component produced by said medium surface displacement and a second phase modulation component produced by spurious sources, and said control voltage applying means comprises, first circuit means responsive to the output signals of said optical detection means and said reference oscillator for separating said reference oscillator signal from phase modulation components, second circuit means connected to said first circuit means and responsive to said phase modulation components for separating said first phase modulation component from said second phase modulation component, and third circuit means for applying a control voltage corresponding to said second phase modulation component to the voltage controlled oscillator of said phase locked loop.

* * * * *

UNITED STATES PATENT AND TRADEMARK OFFICE
CERTIFICATE OF CORRECTION

PATENT NO. : 4,172,382

DATED : October 30, 1979

INVENTOR(S) : John Cornelius Murphy and Raymond C. Cole

It is certified that error appears in the above-identified patent and that said Letters Patent are hereby corrected as shown below:

The assignee's correct name and address is as follows:

The Johns Hopkins University
Baltimore, Maryland

Signed and Sealed this

Tenth Day of March 1981

[SEAL]

Attest:

RENE D. TEGTMEYER

Attesting Officer     Acting Commissioner of Patents and Trademarks